(12) United States Patent
Todasco et al.

(10) Patent No.: US 10,974,733 B2
(45) Date of Patent: *Apr. 13, 2021

(54) VEHICLE USE AND PERFORMANCE RESTRICTIONS BASED ON DETECTED USERS

(71) Applicant: PAYPAL, INC., San Jose, CA (US)

(72) Inventors: Michael Charles Todasco, Santa Clara, CA (US); Dennis Michael Driscoll, Chalfont, PA (US); Jeremy Leigh Cattone, San Jose, CA (US); Amit Reuven Menipaz, San Jose, CA (US)

(73) Assignee: PAYPAL, INC., San Jose, CA (US)

( * ) Notice: Subject to any disclaimer, the term of this patent is extended or adjusted under 35 U.S.C. 154(b) by 115 days.

This patent is subject to a terminal disclaimer.

(21) Appl. No.: 16/248,598

(22) Filed: Jan. 15, 2019

(65) Prior Publication Data
US 2019/0367047 A1 Dec. 5, 2019

Related U.S. Application Data

(63) Continuation of application No. 15/451,159, filed on Mar. 6, 2017, now Pat. No. 10,179,591, which is a
(Continued)

(51) Int. Cl.
*B60W 50/12* (2012.01)
*A61B 5/117* (2016.01)
(Continued)

(52) U.S. Cl.
CPC ............ *B60W 50/12* (2013.01); *A61B 5/00* (2013.01); *A61B 5/117* (2013.01); *A61B 5/6893* (2013.01);
(Continued)

(58) Field of Classification Search
CPC . A61B 5/04012; G07F 17/0057; G07B 15/04; G07B 15/02; H04M 1/72577;
(Continued)

(56) References Cited

U.S. PATENT DOCUMENTS 5,124,920 A * 6/1992 Tamada .................. B60R 25/24
235/382.5
7,314,162 B2 1/2008 Carr et al.
(Continued)

FOREIGN PATENT DOCUMENTS

CN 1460962 12/2003
CN 1666911 9/2005
(Continued)

*Primary Examiner* — Yuri Kan
(74) *Attorney, Agent, or Firm* — Haynes and Boone, LLP (57) ABSTRACT

There are provided systems and methods for vehicle use and performance restrictions based on detected users. A user may check-in to a vehicle so that the vehicle identifies the user, such as through providing identification to the vehicle using biometrics, logins, or other information. Using the identification, the vehicle may determine parameters and restrictions on use of the vehicle by the user. Parameters may include information about the user, such as age, health, or other statistic stored with the identification for the user, and may be utilized to determine restrictions on use of the vehicle by the user, such as a speed of the vehicle and passengers allowed in the vehicle. Restrictions may also be set for the user, including speeds of travel, routes of travel, and usage of media players in the vehicle. The usage of the vehicle may be monitored and enforced using the restrictions.

20 Claims, 6 Drawing Sheets

Related U.S. Application Data continuation of application No. 14/586,798, filed on Dec. 30, 2014, now Pat. No. 9,586,596.

(51) Int. Cl.

| | | |
|---|---|---|
| *G06F 7/00* | (2006.01) | |
| *B60W 40/08* | (2012.01) | |
| *B60W 40/09* | (2012.01) | |
| *G01C 21/36* | (2006.01) | |
| *A61B 5/00* | (2006.01) | |
| *H04W 4/02* | (2018.01) | |
| *H04W 4/48* | (2018.01) | |
| *H04W 4/40* | (2018.01) | |
| *B60W 50/08* | (2020.01) | |
| *B60K 28/02* | (2006.01) | |
| *B60W 50/00* | (2006.01) | |
| *H04W 4/80* | (2018.01) | |
| *H04L 29/08* | (2006.01) | |
| *B60R 25/24* | (2013.01) | |

(52) U.S. Cl.
CPC ............ *B60K 28/02* (2013.01); *B60W 40/08* (2013.01); *B60W 40/09* (2013.01); *B60W 50/082* (2013.01); *G01C 21/36* (2013.01); *G01C 21/3617* (2013.01); *H04W 4/02* (2013.01); *H04W 4/40* (2018.02); *H04W 4/48* (2018.02); *A61B 2503/22* (2013.01); *B60R 25/241* (2013.01); *B60W 50/00* (2013.01); *B60W 2040/0809* (2013.01); *B60W 2040/0881* (2013.01); *B60W 2050/0014* (2013.01); *B60W 2540/043* (2020.02); *B60W 2556/45* (2020.02); *B60W 2556/50* (2020.02); *B60W 2720/10* (2013.01); *H04L 67/18* (2013.01); *H04L 67/22* (2013.01); *H04L 67/306* (2013.01); *H04W 4/023* (2013.01); *H04W 4/025* (2013.01); *H04W 4/027* (2013.01); *H04W 4/80* (2018.02)

(58) Field of Classification Search
CPC ......... G09G 5/00; B60R 25/04; B60R 25/24; G05B 23/0278; G05B 9/02; B60W 50/12; G01F 17/00; B60K 28/063; H04W 4/023; G06F 17/00

USPC ................. 701/48; 705/13; 340/5.52, 932.2
See application file for complete search history.

(56) References Cited

U.S. PATENT DOCUMENTS

| | | | |
|---|---|---|---|
| 8,527,146 B1 | 9/2013 | Jackson et al. | |
| 8,912,924 B2* | 12/2014 | Scofield ................. | G07B 15/04 340/932.2 |
| 9,031,762 B1* | 5/2015 | Bell ....................... | G06F 17/00 345/173 |
| 2003/0204290 A1* | 10/2003 | Sadler .................... | B60R 25/04 701/1 |
| 2006/0255911 A1* | 11/2006 | Taki ....................... | B60R 25/24 340/5.72 |
| 2009/0024309 A1 | 1/2009 | Crucs | |
| 2011/0032093 A1 | 2/2011 | Miller et al. | |
| 2011/0137520 A1* | 6/2011 | Rector ............. | H04M 1/72577 701/36 |
| 2012/0001876 A1* | 1/2012 | Chervenka ............... | G09G 5/00 345/204 |
| 2012/0268235 A1* | 10/2012 | Farhan ..................... | G05B 9/02 340/3.1 |
| 2013/0289799 A1 | 10/2013 | Johnson et al. | |
| 2014/0129301 A1* | 5/2014 | Van Wiemeersch ... | G07B 15/02 705/13 |
| 2014/0358376 A1 | 12/2014 | Phelan | |
| 2014/0361871 A1* | 12/2014 | Silva .................. | A61B 5/04012 340/5.52 |
| 2015/0021113 A1* | 1/2015 | Lefevbre ............... | B60K 28/063 180/272 |
| 2015/0024786 A1* | 1/2015 | Asrani .................. | H04W 4/023 455/456.4 |

FOREIGN PATENT DOCUMENTS

| | | |
|---|---|---|
| CN | 1853993 | 11/2006 |
| CN | 101359407 | 2/2009 |
| CN | 101596895 | 12/2009 |
| CN | 201442569 | 4/2010 |
| CN | 101902619 | 12/2010 |
| CN | 102529888 | 7/2012 |
| CN | 103761774 | 4/2014 |

\* cited by examiner

VEHICLE USE AND PERFORMANCE RESTRICTIONS BASED ON DETECTED USERS

CROSS REFERENCE

This application is a continuation of U.S. patent application Ser. No. 15/451,159, filed Mar. 6, 2017, which is a continuation of U.S. patent application Ser. No. 14/586,798, filed Dec. 30, 2014 and issued as U.S. Pat. No. 9,586,596, all of which are incorporated hererin by reference in their entirety.

TECHNICAL FIELD

The present application generally relates to vehicle use and performance restrictions based on detected users and more specifically to detecting a user within and/or utilizing a vehicle in order to determine, communicate, place, authorize, and/or remove restrictions on the vehicle's use and performance while under the control of the user.

BACKGROUND

An owner or operator of a vehicle may offer their vehicle for use by another party, such as a parent providing use of their vehicle to their child or a friend providing their vehicle to another friend. However, the user who maintains control of their vehicle may wish to enforce certain restrictions on use of the vehicle. For example, a recently licensed driver may be prevented from driving passengers until of a certain age or after a certain time period of driving. In other embodiments, the vehicle may include onboard systems that the owner may wish to restrict, such as automatic toll payments and satellite radio or other media requiring payment. In order to enforce these uses of the vehicle, the user exerting control over the vehicle may inform the other operating user of restrictions on use of the vehicle. However, this may not prevent the operating user from using the vehicle in unauthorized manners. Moreover, the user exerting control over the vehicle may not have methods to monitor usage of the vehicle, or may only be informed of unauthorized usage substantially after the time of the unauthorized usage.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

Provided are methods that provide vehicle use and performance restrictions based on detected users. Systems suitable for practicing methods of the present disclosure are also provided.

In various embodiments, an owner, operator, or other user exerting control over a vehicle may provide use of the vehicle to another user. For example, the vehicle may belong to a parent or friend that offers their vehicle for use to an associated person. The vehicle may also belong to a third party that is allowing use of the vehicle to a service shop, valet service, or other service provider while the third party is removed from the vehicle. The vehicle may also belong to a service that provides use of the vehicle to other users, such as a company car, rental vehicle, a fleet vehicle, and/or a car share service. The vehicle may also correspond to vehicles other than a car, such as a boat, motorcycle, airplane, bus, motorhome, helicopter, water craft, drone, etc. When using a vehicle offered to the user, the user may be detected in the vehicle so that the vehicle identifies the user when the user is inside the vehicle and/or utilizing the vehicle. For example, the user may provide some information to a device associated with the vehicle. The user may log in to a device in the vehicle, such as a center console computing device or heads up display by providing a log in credential to the device (e.g., a log in credential identifying a user account for the user, for example, a name and PIN/password associated with the user account). A proxy identification may also be used, such as a RFID tag or NFC device. The user may also be detected when the vehicle's device connects to a communication device of the user. In such embodiments, the user may have a mobile/smart phone, wearable computing device (e.g., eyeglasses or wristwatch with processing features), tablet computer, or other user device. The vehicle's device and the device of the user's communication device through a short range communication protocol, such as Bluetooth, WiFi, Bluetooth Low Energy, LTE Direct, infrared, radio, near field, or other communication protocol. The device for the vehicle may correspond to a dashboard or other onboard computing device, or may correspond to a device associated with the user exerting control over the vehicle, such a mobile/smart phone, tablet computer, wearable computing device, or other user device. Thus, once the vehicle's device and the user's communication device connect, the user may be identified and checked-in to the vehicle. Authorization may also be tied to a user account or anonymous token, which may be shared by more than one user. Thus, the aforementioned user detected in the vehicle may correspond more generally to a plurality of users sharing an identifier or identification information.

The user may also be detected through biometrics and biometric reading devices utilized by the vehicle device, such as a fingerprint scanner (e.g., a fingerprint scanner on a door handle, steering wheel, or input device of the vehicle device), eye/retinal scanner, DNA reader, breathalyzer, etc. Once the user is detected in the vehicle, the vehicle's device may set or load parameters for the user and access and/or determine restrictions on use of the vehicle by the user. In various other embodiments, the user exerting control of the vehicle may set standardized restrictions for the vehicle, or may set restrictions based on user parameters (e.g., age, health, etc.). The user parameters may also be based on information associated with the user, such as subscriptions, frequency of use, or other user profile information about the user. In such embodiments, the user may not need to be personally detected and/or identified, and a general detection of the user may be sufficient. Thus, the user may be more generally identified than specifically identified, through just a general state of being a user different from the user exerting control over the vehicle, to more detailed parameters of the user (e.g., age, height, weight, etc.).

Once the user is detected as utilizing the vehicle, restrictions for the user may be determined. The restrictions may be set for all use of the vehicle by the user or may vary based on use of the vehicle and/or during use of the vehicle. Thus, authorizations to use the vehicle and restrictions placed on use of the vehicle may vary during use of the vehicle (e.g., if the user utilizes the vehicle in an unauthorized manner, such as later than intended). The authorizations may be set on a single or limited use basis, such as a restriction to prevent or allow usage of a vehicle entertainment system on a one time basis, or use of the vehicle's payment application on a once per week basis for fuel. The restrictions may be set for the user individually, for all users, and/or based on parameters of the user (e.g., age, height, weight, health, etc.). The restrictions may be set by the user exerting control of the vehicle and may be specific to the vehicle or to all or part of the vehicles the user has control over. The restrictions may also follow the user so that other vehicle the user utilizes may inherit the restrictions from the first vehicles use, such that the restrictions and/or authorizations may be restored automatically to a ne vehicle. The restrictions may be determined from information stored to the vehicle's device, a server, or a device for the user (e.g., a communication device, keyfob with a readable memory, etc.).

The restrictions may also be set by a guardian of the user operating the vehicle, such as a parent of the user. As used herein, "owner" refers generally to anyone who exerts control over the vehicle or sets restrictions for use of the vehicle for the user. The restrictions may be retrieved or may be determined based on the parameters of the user. The restrictions may correspond to some aspect of use or performance of the vehicle and/or onboard devices of the vehicle. For example, restriction may be associated with a travel route taken by the vehicle, a travel speed of the vehicle, a use of an onboard computing feature of the vehicle (e.g., a payment application/module, a satellite radio unit, etc.), and/or a use of a service associated with the vehicle (e.g., OnStar®, toll road payments, etc.). For example, the restrictions may include one or more of a restriction on a travel distance using the vehicle, travel route using the vehicle, travel speed using the vehicle, an item payment made using an onboard computing device of the vehicle, a toll payment made using the onboard computing device of the vehicle, media playback using the onboard computing device of the vehicle, radio or media stations available using the onboard computing device of the vehicle, use of a communication application of the onboard computing device of the vehicle, a number of other passengers in the vehicle, an age of the other passengers in the vehicle, an identity of the other passengers in the vehicle, and an insurance policy associated with the vehicle.

Once the restrictions are accessed and/or determined, the restrictions may be enforced on usage of the vehicle by the user. Thus, the user may be prevented from utilizing the vehicle in a way that violates the restrictions. For example, the user may be prevented from utilizing a satellite radio of the vehicle or from performing payments using a payment application of the vehicle. However, in certain embodiments, restrictions on travel speed, travel route, or usage of onboard features of the vehicle may be unsafe for emergency reasons. Thus, the usage of the vehicle may be monitored and reported to the party exerting control over the vehicle and/or a guardian of the user. The user operating the vehicle may be alerted of the restrictions placed on the vehicle, such as through an onboard device of the vehicle and/or through the user's communication device. Moreover, if the user begins to use the vehicle in an unauthorized manner, the user may be alerted of the unauthorized usage, for example, to allow the user to rectify their usage. Additionally, the restrictions on the use and/or performance of the vehicle may also be dependent on the passengers in the vehicle and travelling with the user operating the vehicle. For example, if a parent is with their child and operating the vehicle, a restriction on allowing the child to travel with passengers under an age limit may be lifted. Moreover, the user exerting control of the vehicle may allow for usage of a payment module associated with the vehicle to pay for fuel, tolls, or other items/services if the user exerting control of the vehicle is within the vehicle during usage by another party. Thus, the vehicle may also detect other users in the vehicle.

Figure 1:
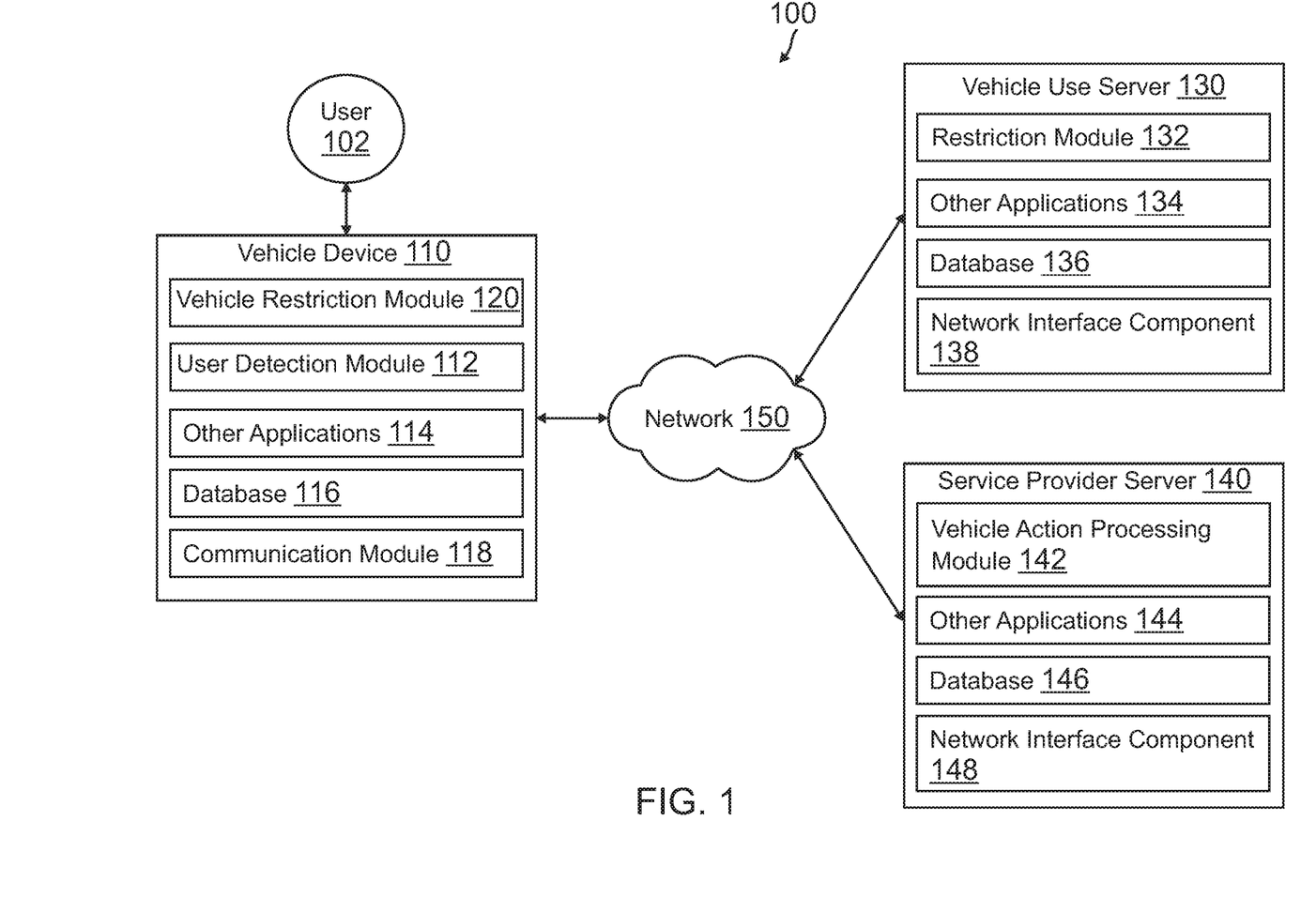
FIG. 1 is a block diagram of a networked system suitable for implementing the processes described herein, according to an embodiment.

FIG. 1 is a block diagram of a networked system 100 suitable for implementing the processes described herein, according to an embodiment. As shown, system 100 may comprise or implement a plurality of devices, servers, and/or software components that operate to perform various methodologies in accordance with the described embodiments. Exemplary device and servers may include device, stand-alone, and enterprise-class servers, operating an OS such as a MICROSOFT® OS, a UNIX® OS, a LINUX® OS, or other suitable device and/or server based OS. It can be appreciated that the devices and/or servers illustrated in FIG. 1 may be deployed in other ways and that the operations performed and/or the services provided by such devices and/or servers may be combined or separated for a given embodiment and may be performed by a greater number or fewer number of devices and/or servers. One or more devices and/or servers may be operated and/or maintained by the same or different entities.

System 100 includes a user 102, a vehicle device 110, a vehicle use server 130, and service provider server 140 in communication over a network 150. User 102, such as a driver or operator of a vehicle corresponding to vehicle device 110, may be detected and identified by vehicle device 110. For example, user 102 may connect a device to vehicle device 110, may log in to vehicle device 110, and/or may be identified by user parameters or biometrics. Once detected, restrictions for use of the vehicle may be accessed and/or determined. The restrictions may be set with vehicle device 110 and/or vehicle use server 130. Various restrictions may include use of services offered by service provider server 140 by vehicle device 110.

Vehicle device 110, vehicle use server 130, and service provider server 140 may each include one or more processors, memories, and other appropriate components for executing instructions such as program code and/or data stored on one or more computer readable mediums to implement the various applications, data, and steps described herein. For example, such instructions may be stored in one or more computer readable media such as memories or data storage devices internal and/or external to various components of system 100, and/or accessible over network 150.

Vehicle device 110 may be implemented using any appropriate hardware and software configured for wired and/or wireless communication with vehicle use server 130 and/or service provider server 140. In various embodiments, vehicle device 110 may be implemented as a device for use in a vehicle corresponding to vehicle device 110, such as a personal computer (PC), a smart phone, laptop computer, wristwatch with appropriate computer hardware resources, eyeglasses with appropriate computer hardware (e.g. GOOGLE GLASS®) and/or other types of computing devices capable of transmitting and/or receiving data, such as an IPADI from APPLE®, which may provide processing services for the vehicle. Vehicle device 110 may also be implemented as a device physically attached to and/or connected to the vehicle, such as a dashboard or central console computing system, a heads up display with attached processing devices, and/or a similar in vehicle on board computing system. Although a vehicle device is shown, the vehicle device may be managed or controlled by any suitable processing device. Although only one vehicle device is shown, a plurality of vehicle devices may function similarly. Moreover, in various embodiments, one or more of the applications, processes, and/or features discussed below in reference to vehicle device 110 may be included in a communication device connected to vehicle device 110. Furthermore, the processes and features of restrictions module 132 of vehicle use server 130 may be implemented on vehicle device 110 instead.

Vehicle device 110 of FIG. 1 may contain a vehicle restriction module 120, a user detection module 112, other applications 114, a database 116, and a communication module 118. User detection module 112, on board applications 140, and other applications 114 may correspond to processes, procedures, and/or applications, for example, a software program, executable by a hardware processor. In other embodiments, vehicle device 110 may include additional or different modules having specialized hardware and/or software as required.

Vehicle restriction module 120 may correspond to one or more processes to execute modules and associated devices of vehicle device 110 to set, access, and/or determine restrictions on use of a vehicle by user 102 and enforce those restrictions with respect to the vehicle corresponding to vehicle device 110. In this regard, vehicle restriction module 120 may correspond to specialized hardware and/or software utilized by vehicle device 110 to set, access, and/or determine restriction for user 102 and access and/or determine those restrictions once user 102 is detected by user detection module 112, as will be explained in more detail with respect to user detection module 112. For example, vehicle restriction module 120 may receive input having restrictions for user 102, such as through a user interface or from a device connected to vehicle device 110. The restrictions may be set by an entity exerting control over the vehicle corresponding to vehicle device 110. The restrictions may also be set by the entity with vehicle user server 130. The restrictions may be loaded to vehicle device 110 and stored with vehicle device 110, for example, in database 116 stored to a non-transitory memory of vehicle device 110. The restrictions may also be accessed from vehicle use server 130 on detection and identification of user 102. The restrictions for use of the vehicle by user 102 may be set by user 102, a guardian or entity associated with user 102 (e.g., a parent, company, rental agency, etc.), and/or by a person or entity exerting control or ownership of the vehicle (e.g., an owner of the vehicle or authorized operator/controller of the vehicle, such as a rental agent, lessee of the vehicle, dealership associated with the vehicle, etc.).

A restriction on use of a vehicle associated with vehicle device 110 by user 102 may correspond to authorized and/or unauthorized use of the vehicle and the vehicle's associated services and computing systems. In this regard, a restriction on use of the vehicle by user 102 may be associated with a travel route taken by the vehicle, a travel speed of the vehicle, a use of an onboard computing feature of the vehicle (e.g., a payment application/module, a satellite radio unit, etc.), and/or a use of a service associated with the vehicle (e.g., OnStar®, toll road payments, etc.). For example, the restrictions may include one or more of a restriction on a travel distance using the vehicle, travel route using the vehicle, travel speed using the vehicle, a time of travel or use of the vehicle (e.g., no use before or after a time of day), an item payment made using an onboard computing device of the vehicle, a toll payment made using the onboard computing device of the vehicle, media playback using the onboard computing device of the vehicle, radio or media stations available using the onboard computing device of the vehicle, use of a communication application of the onboard computing device of the vehicle, a number of other passengers in the vehicle, an age of the other passengers in the vehicle, an identity of the other passengers in the vehicle, and an insurance policy associated with the vehicle.

A restriction on use of the vehicle may be specific to one or more of user 102 and the vehicle. For example, a restriction may be placed on use of any vehicle that user 102 utilizes, such as preventing user 102 from travelling with passengers if user 102 has not met their state's age or driving experience requirements. Alternatively, the restriction may also be placed on the vehicle particularly associated with vehicle device 110, such as prevention of use of toll payment services for the vehicle by any operators of the vehicle aside from an owner of the vehicle (e.g., to prevent payments of tolls by the owner when a friend, co-worker, or other family member is utilizing the vehicle). The restriction may also be a combination of the two, thereby creating a restriction for use of the particular vehicle associated with vehicle device 110 by only user 102 (e.g., to prevent user 102 from utilizing a satellite radio unit of the vehicle while still allowing other user's to use the aforementioned satellite radio unit).

Once user 102 is identified, the restrictions for user 102 may be accessed and/or determined by vehicle restriction module 120 from database 116 and/or vehicle user server 130, as previously discussed. For example, the restrictions may be directly linked to an identity of user 102 such that the restrictions are loaded by vehicle restriction module 120 using the identity of user 102 directly. In other embodiments, the restrictions for user 102 may be required to be determined based on the identity of user 102 and/or the parameters for user 102 (e.g., age, health, height, weight, etc.). Thus, where a restriction may be associated with an age, health, height, or weight of a user utilizing the vehicle associated with vehicle device 110, the restriction may be determined once the parameters for user 102 are accessed/determined by vehicle restriction module 120. Restrictions for use of the vehicle based on parameters of user 102 may correspond to speed of travel of the vehicle, travel route of the vehicle, authorized use/operating the vehicle (e.g., no operation of the vehicle if the user is above or below a certain age, height, weight, etc.), operation of onboard services and computing functions of the vehicle, or other restriction as previously discussed.

Once the restrictions are loaded by vehicle restriction module 120, vehicle restriction module 120 may communicate the restrictions to user 102 and/or enforce the restriction on usage of the vehicle associated with vehicle device 110. In this regard, vehicle restriction module 120 may include hardware and/or software to communicate the restrictions to user 102 through a device interface of vehicle device 110 and/or to a communication device for user 102. The restrictions may be displayed to user 102 with their corresponding restricted usage of the vehicle. Thus, user 102 may be informed about the restricted usage of the vehicle. The usage of the vehicle may be restricted by vehicle restriction module 120, such as prevention of usage of one or more onboard systems, use, and/or performance of the vehicle. However, restriction on usage of the vehicle may be unsafe in certain embodiments (e.g., limiting travel routes or travel speed). In such embodiments, user 102 may only be informed of the restriction and the vehicle's use or performance may not be limited.

Further, vehicle restriction module 120 may monitor and store user 102's actual usage of the vehicle and alert user 102 and/or the owner that user 102 is utilizing the vehicle and/or the vehicle's associated systems/services in an unauthorized manner. If user 102 is utilizing the vehicle in a manner that violates the restrictions, user 102 may be alerted by vehicle restriction module 120, such as through vehicle device 110 (e.g., a displayable or audible notification/alert), or to a communication device for user 102. Additionally, vehicle restriction module 120 may alert the person/entity exerting control over the vehicle that user 102 is utilizing the vehicle in an unauthorized manner. Such alerts to the person/entity exerting control over the vehicle may be communicated to a device associated with the person/entity, or may be stored in database 116 or vehicle use server 130 for retrieval by the person/entity at a later time.

User detection module 112 may correspond to one or more processes to execute modules and associated specialized hardware of vehicle device 110 to detect user 102 as in, nearby, or otherwise using a vehicle associated with vehicle device 110 and determine an identity for user 102. In this regard, user detection module 112 may correspond to specialized hardware and/or software utilized by vehicle device 110 to first detect that user 102 is operating or attempting to operate the vehicle. In order to detect user 102, user detection module 112 may utilize one or more sensors, such as a door sensor, weight sensor, pressure sensor, key detector or ignition switch, biometric scanner, log in process, device connection/communication module, camera, microphone, and/or proximity sensor. For example, user$^{102}$ may be detected when user 102 opens a door to utilize the vehicle, sits in a seat associated with the vehicle, or places a key in an ignition or in proximity to the vehicle. Once user 102 is detected as in or nearby the vehicle, user detection module$^{112}$ may determine an identity for user 102 and provide the identification information to vehicle restriction module 120 in order to determine one or more restrictions for use of the vehicle, as previously discussed. For example, a camera attached to or associated with the vehicle may capture an image of user 102 and communicate the image to a service provider for determining the identity of user 102 corresponding with the image. In another example, a microphone may capture voice of user 102, where identification of user 102 may be through voice recognition means.

User detection module 112 may determine an identification for user 102 by detecting and connecting with a device associated with user 102 and receiving identification information for user 102 (e.g., a name, identifier, etc.). As previously discussed, vehicle device 110 may be located in, attached and connected to, and/or associated with a vehicle. User 102 may utilize a communication device (e.g., a mobile/smart phone, laptop or tablet computer, wearable computing device, or other device) to connect to vehicle device 110 in order to provide identification information to vehicle device 110. The connection between the user device and vehicle device 110 may utilize short range wireless communications of vehicle device 110 to establish the connection. For example, user detection module 112 may transmit an identifier such as a Universally Unique Identifier (UUID) to the device. If user 102's device receives a request to establish the connection with vehicle device 110 and responds with an identifier for user 102, vehicle device 110 to ramp up in power and create a connection between user 102's device and vehicle device 110. The identifier for vehicle device 110 transmitted to user 102's device may be included in the received identifier for user 102 and/or user 102's device for example, the identifier may be transmitted with, concatenated with, or otherwise bundled with the identifier in the received token. In such embodiments, user detection module 112 may utilize communication module 118 of vehicle device 110 to receive the token from user 102's device, and process the token to establish a connection and determine an identity for user 102. In various embodiments, user detection module$^{112}$ may execute in the background of an operating system of vehicle device 110 and be configured to establish connections, using communication module 118 of vehicle device 110, with user 102's device. However, in other embodiments, user detection module 112 may connect with user 102's device on command by user 102.

Thus, vehicle device 110 may uniquely transmit the request to establish the connection with vehicle device 110 as a short range wireless communication (e.g. a BLE protocol communication) including a "wake up" process for user 102's device and a token for vehicle device 110 transmitting the request. In other embodiments, the request and/or connection may utilize near field communication, radio communication, infrared communication, or Bluetooth communication. Additionally, although vehicle device 110 may utilize BLE protocol communications to effectuate an "always on" type service where the UUID and "wake up" process are transmitted continuously by vehicle device 110, other communication protocols used to provide an "always on" service may include QUALCOMM® LTE Direct or similar device-to-device communication technology. BLE and LTE Direct may both be utilized to provide discovery of nearby devices to vehicle device 110 and establishment of a connection for identification of user 102.

In various embodiments, vehicle device 110 may also request a log in from user 102 that detects and identifies user 102, for example, using an input device associated with vehicle device 110 (e.g., an input interface of a display module for vehicle device 110). In such embodiments, user 102 may provide an identifier, user account name, password, and/or PIN directly to vehicle device 110 without the use of the aforementioned device in possession of user 102. Once user 102 logs in to user detection module 112, an identity of user 102 may be accessed (e.g., from database 116) or determined using vehicle user server 130 or another service provider.

User 102 may also be identified by vehicle device 110 using biometrics and biometric reading devices utilized by vehicle device 110, such as a fingerprint scanner (e.g., a fingerprint scanner on a door handle, steering wheel, or input device of the vehicle device), eye/retinal scanner, DNA reader, breathalyzer, etc. User 102 may be detected using one of the aforementioned sensors or may be detected using the biometric scanner(s) associated with user detection module 112. Once a biometric reading of user 102 is received by user detection module 112, user detection module[112] may determine and identity of user 102 through accessing identification information associated with the biometric read to one or more of database 116 and/or vehicle use server 130. Thus, identification information may be entered to vehicle using an interactive touch screen, a keyboard, a mouse, a biometric reader, or other input device for vehicle device 110. The identification information may further be stored with information for user 102, such as the identifier for user 102, the log in information of user 102, and/or the biometric reading of user 102.

In various embodiments, one or more features of vehicle restriction module 120 and/or user detection module 112 may be incorporated in the same module so as to provide their respective features in one module.

Vehicle device 110 includes other applications 114 as may be desired in particular embodiments to provide features to vehicle device 110. For example, other applications 114 may include security applications for implementing client-side security features, programmatic client applications for interfacing with appropriate application programming interfaces (APIs) over network 150, or other types of applications. Other applications 114 may also include email, texting, voice and IM applications that allow an owner/operator of a vehicle corresponding to vehicle device 110 to send and receive emails, calls, texts, and other notifications through network 150. Such communication applications may also correspond to mobile, satellite, wireless Internet, and/or radio communication applications connected to car services, such as OnStar®, which may be configured to interact with one or more other vehicle devices functioning similar to vehicle device 110 in order to facilitate mapping, communication, and/or emergency services. Other applications 114 may include payment applications and/or services, for example, applications/services that may provide payments for car servicing and/or cleaning, purchases made by a user in the vehicle (e.g., user 102 and/or a person/entity exerting control over the vehicle), and/or tolls, gas, or other travel payments required during use of the vehicle. Other applications 114 may include mapping and/or GPS applications configured to display location information to user 102. In various embodiments, other applications 114 may include financial applications, such as banking, online payments, money transfer, or other financial applications. Other applications 114 may contain other software programs, executable by a processor, including a graphical user interface (GUI) configured to provide an interface for vehicle device 110 to the user. As previously discussed, other applications 114 may be limited, restricted, or otherwise managed by restrictions set for use/performance of the vehicle associated with vehicle device 110 by a person/entity exerting control over the vehicle. For example, use of communication, radio, mapping, payment, and/or GUI services provided by other applications 114 may be limited by the restrictions.

Vehicle device 110 may further include database 116 which may include, for example, identifiers such as operating system registry entries, cookies associated with vehicle restriction module 120, user detection module 112, and/or other applications 114, identifiers associated with hardware of vehicle device 110, or other appropriate identifiers, such as identifiers used for payment/user/device authentication or identification. Database 116 may store identification information for one or more users, including user 102, as well as information necessary to access or determine the identification information when user 102 utilizes the vehicle associated with vehicle device 110 (e.g., a identifier, log in information, a biometric reading, etc.). Database 116 may further store restriction for use with the vehicle associated with vehicle device 110. The restrictions may be associated or stored with the identification information for retrieval when a user is detected. However, in other embodiments, the restrictions may be accessed or determined using vehicle use server 130. In such embodiments, database 116 may only store received identification information determined by user detection module 112 and used by vehicle restriction module 120 to determine restrictions. In one embodiment, identifiers in database 116 may be used by service provider server 140 to associate vehicle device 110 with a particular account maintained by service provider server 140.

Vehicle device 110 includes at least one communication module 118 adapted to communicate with vehicle use server 130, service provider server 140, and/or a device for user 102. In various embodiments, communication module 118 may include a DSL (e.g., Digital Subscriber Line) modem, a PSTN (Public Switched Telephone Network) modem, an Ethernet device, a broadband device, a satellite device and/or various other types of wired and/or wireless network communication devices including microwave, radio frequency, infrared, Bluetooth, and near field communication devices. Communication module 118 may communicate directly with user 102's device using short range communications, such as Bluetooth Low Energy, LTE Direct, radio frequency, infrared, Bluetooth, and near field communications.

Vehicle use server 130 may be maintained, for example, by a service provider, which may manage restrictions for a vehicle associated with vehicle device 110. For example, vehicle use server 130 may correspond to or be associated with a person or entity exerting control of the vehicle. In this regard, vehicle use server 130 includes one or more processing applications which may be configured to interact with vehicle device 110 and/or service provider server 140 to provide determination and management of restrictions and enforcement of such restrictions on the vehicle. Although only one server is shown, a plurality of servers and/or associated devices may function similarly. Although vehicle use server 130 is described as a server device, in various embodiments, vehicle use server 130 may function as a specialized device for the vehicle. Thus, although vehicle use server 130 is shown as separate from vehicle device 110, the below described modules, hardware, and functions may be included within vehicle device 110.

Vehicle use server 130 of FIG. 1 includes a restrictions module 132, other applications 134, a database 136, and a network interface component 138. Restrictions module 132 and other applications 134 may correspond to executable processes, procedures, and/or applications with associated hardware. In other embodiments, vehicle use server 130 may include additional or different modules having specialized hardware and/or software as required.

Restrictions module 132 may correspond to one or more processes to execute modules and associated devices of vehicle use server 130 to set, manage, and/or access/determine restrictions. In this regard, restrictions module 132 may correspond to specialized hardware and/or software utilized by vehicle use server 130 with vehicle device 110 to set and/or manage restrictions for user 102 and/or a vehicle associated with vehicle device 110. Restrictions for user 102 and/or the vehicle may be set and managed by user 102, a person/entity associated with user 102 (e.g., a guardian for user 102, a workplace for user 102 providing one or more vehicles to user 102, a rental company used by user 102, etc.), and/or a person/entity exerting control over the vehicle associated with vehicle device 110. Restrictions may be entered to restrictions module 132 of vehicle use server 130 by vehicle device 110 and/or by another device/server when the restrictions are set for user 102 and/or the vehicle. Restrictions module[132] may associate received restrictions with identification information for user 102 so that the restrictions may be accessed and/or determined when identification information for user 102 is received by vehicle device 110. The restrictions may be stored to database 136 with the identification information. In various embodiments, the restrictions may be communicated to vehicle device 110 for storage as well.

As previously discussed, restrictions for use of a vehicle associated with vehicle device 110 may correspond to a restriction on the use of performance of the vehicle, of an onboard module or application of the vehicle, and/or of a service associated with the vehicle. Further, the restrictions may correspond to one or more restrictions for user 102 (e.g., all vehicle user 102 may utilize), for the vehicle (e.g., all or some subset of users utilizing a vehicle), and/or for user 102's use of the vehicle. The restrictions may be accessed by restrictions module 132 from database 136 when vehicle device 110 communicates identification information for user 102 to vehicle use device 130. In other embodiments, the restrictions may be accessed by vehicle device 110 from database 116 by vehicle restriction module 120, as previously discussed. Moreover, the restrictions may be determined by one or more of vehicle restriction module 120 and restrictions module 132 using parameters for user 102, such as an age, weight, height, health, or other user parameter or preference. Such user parameters and preferences may be determined by one or more of vehicle restriction module 120 and restrictions module 132 using the user identification information determined using user detection module 112.

In various embodiments, vehicle use server 130 includes other applications 134 as may be desired in particular embodiments to provide features to vehicle use server 130. For example, other applications 134 may include security applications for implementing server-side security features, programmatic server applications for interfacing with appropriate application programming interfaces (APIs) over network 150, or other types of applications. Other applications 134 may contain software programs, executable by a processor, including a graphical user interface (GUI), configured to provide an interface to a user.

Vehicle use server 130 may further include database 136 which may include, for example, identifiers such as operating system registry entries, cookies associated with restrictions application 132 and/or other applications 134, identifiers associated with hardware of vehicle use server 130, or other appropriate identifiers. Database 136 may include restrictions set for use of a vehicle associated with vehicle device 110, as well as information necessary to access or determine such restrictions on use of the vehicle by user 102. For example, database 136 may further include identification information for user 102, as well as identifiers for user 102, a device for user 102, and/or an account for user 102. Database 136 may store log in information and/or biometric information for user 102.

Vehicle use server 130 includes at least one network interface component 138 adapted to communicate with vehicle device 110 and/or service provider server 140 over network 150. In various embodiments, network interface component 138 may include a DSL (e.g., Digital Subscriber Line) modem, a PSTN (Public Switched Telephone Network) modem, an Ethernet device, a broadband device, a satellite device and/or various other types of wired and/or wireless network communication devices including microwave, radio frequency, infrared, Bluetooth, and near field communication devices.

Service provider server 140 may be maintained, for example, by an online service provider, which may provide a service associated with use of performance of a vehicle associated with vehicle device 110. For example, service provider server 140 may correspond to a payment service provider, a merchant (e.g., a gas station, car maintenance company, restaurant, etc.), a transportation service provider (e.g., a toll road management company), a media provider (e.g., a radio provider, a messaging service, etc.), a service provider managing an onboard application/service of the vehicle (e.g., a messaging, phone, mapping, etc., service provider), or other type of service provider. In this regard, service provider server 140 includes one or more processing applications which may be configured to interact with vehicle device 110 and/or vehicle use server 130. In one example, service provider server 140 may be provided by PAYPAL®, Inc. of San Jose, Calif., USA. Although only one server is shown, a plurality of servers and/or associated devices may function similarly. Although service provider server 140 is described as a server device, in various embodiments, service provider server[140] may function as a device (e.g., a device for a gas station).

Service provider server 140 of FIG. 1 includes a vehicle action processing module 142, other applications 144, a database 146, and a network interface component 148. Vehicle action processing module 142, and other applications 144 may correspond to processes, procedures, and/or applications, for example, a software program, executable by a hardware processor. In other embodiments, service provider server 140 may include additional or different modules having specialized hardware and/or software as required.

Vehicle action processing module 142 may correspond to one or more processes to execute modules and associated devices to process some action taken with regard to use of a vehicle associated with vehicle device 110. In this regard, vehicle action processing module 142 may correspond to specialized hardware and/or software utilized by vehicle action processing module 142 to receive a request to process an action by user 102 when user 102 is utilizing the vehicle associated with vehicle device 110. For example, an action processed by vehicle action processing module 142 may correspond to a transaction for processing by vehicle action processing module 142, such as a payment to service provider server 140 or a merchant. Other actions may correspond to a request for receipt or access of media, including satellite radio stations, messaging services between users, and/or other forms of audio, video, or audiovisual media content exchange (e.g., receipt and presentation of video on vehicle device 110, a mapping application of vehicle device 110, etc.). Actions may also be associated with use of the vehicle associated with vehicle device 110, such as toll payments, vehicle maintenance requirements, fuel requirements and payments, or other use/performance of the vehicle. Vehicle action processing module 142 may process the action if the action is received from vehicle device 110. For example, where vehicle restriction module 120 has determined that no restriction is placed on the action, vehicle device 110 may communicate the action to service provider server 140 for processing. However, vehicle action processing module 142 may also enforce restrictions on the use and performance of the vehicle. Thus, if the action is received from vehicle device 110 by vehicle action processing module 142, vehicle action processing module 142 may determine if a restriction is placed on the action from one or more of vehicle device 110 and vehicle use server 130 prior to processing. Vehicle action processing module 142 may then process the action in accordance with the restriction (e.g., choose to not process the action or process the action with the restrictions set on the action, such as a spending limit, requirement for a type of gas, vehicle use requirements prior to usage of mapping or messaging services of vehicle device 110, etc.).

In various embodiments, service provider server 140 includes other applications 144 as may be desired in particular embodiments to provide features to service provider server 140. For example, other applications 144 may include security applications for implementing server-side security features, programmatic server applications for interfacing with appropriate application programming interfaces (APIs) over network 150, or other types of applications. Other applications 144 may contain software programs, executable by a processor, including a graphical user interface (GUI), configured to provide an interface to a user.

Additionally, service provider server 140 includes database 146. As previously discussed, user 102 and/or a person/entity exerting control over a vehicle associated with vehicle device 110 may establish one or more payment accounts with service provider server 140. User accounts in database 146 may include user information, such as name, address, birthdate, payment/funding information, additional user financial information, and/or other desired user data. Account holders may link to their respective accounts through a user and/or device identifier. Thus, when an identifier is transmitted to service provider server 140, e.g. from vehicle device 110 and/or vehicle use server 130, an account may be found. In other embodiments, user 102 and/or the person/entity exerting control over the vehicle may not have previously established an account and may provide other information to service provider server 140 to process actions by vehicle action processing module 142, as previously discussed. Additionally, database 146 may store received information, such as actions for processing, user identification information, and/or restrictions placed on actions processed by vehicle action processing module 142.

In various embodiments, service provider server 140 includes at least one network interface component 148 adapted to communicate vehicle device 110 and/or vehicle use server 130 over network 150. In various embodiments, network interface component 148 may comprise a DSL (e.g., Digital Subscriber Line) modem, a PSTN (Public Switched Telephone Network) modem, an Ethernet device, a broadband device, a satellite device and/or various other types of wired and/or wireless network communication devices including microwave, radio frequency (RF), and infrared (IR) communication devices.

Network 150 may be implemented as a single network or a combination of multiple networks. For example, in various embodiments, network 150 may include the Internet or one or more intranets, landline networks, wireless networks, and/or other appropriate types of networks. Thus, network 150 may correspond to small scale communication networks, such as a private or local area network, or a larger scale network, such as a wide area network or the Internet, accessible by the various components of system 100.

Figure 2A:
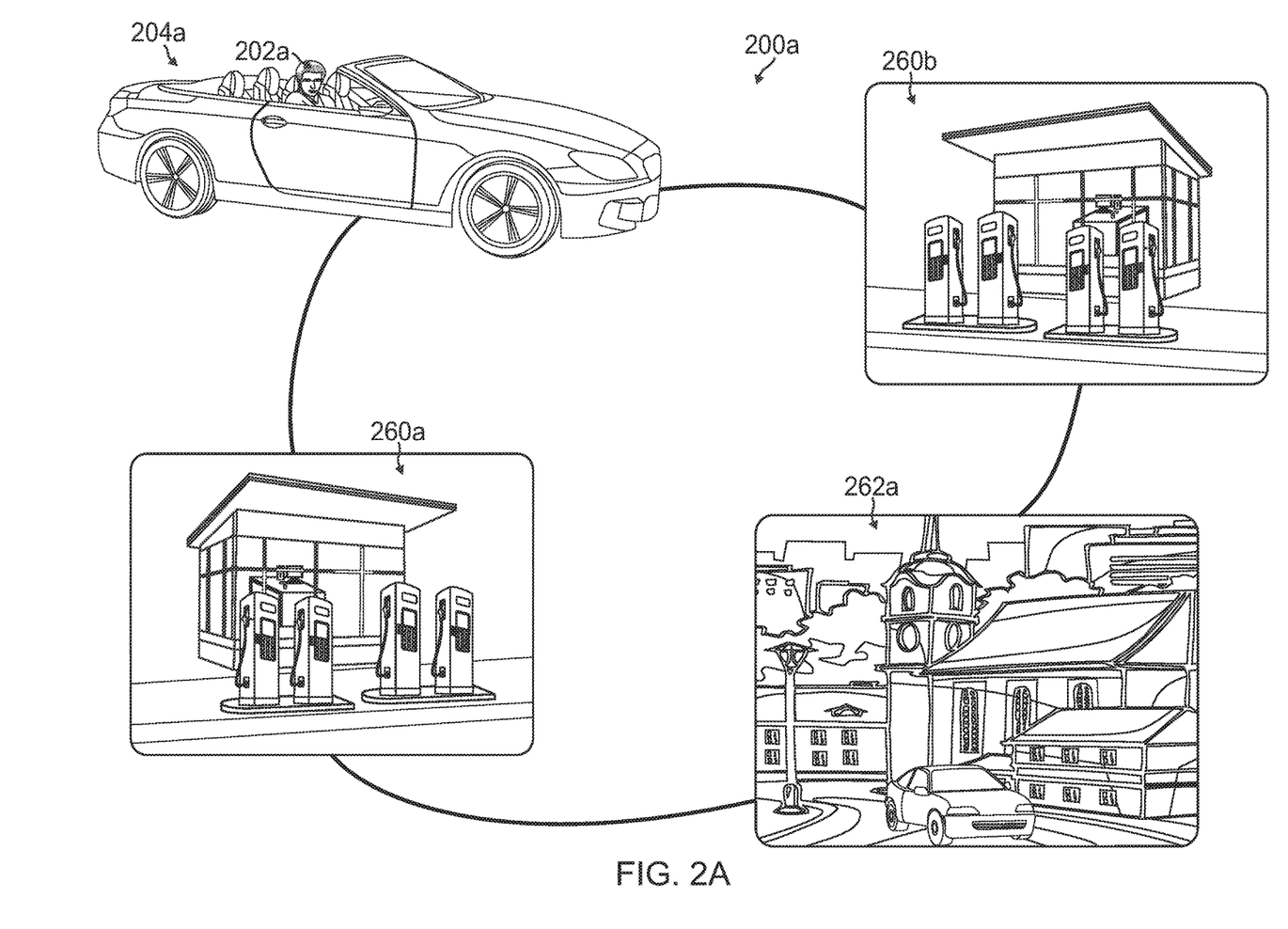
FIG. 2A is an exemplary environment having a vehicle with an operating user travelling to an endpoint by one of two travel routes, according to an embodiment.

FIG. 2A is an exemplary environment having a vehicle with an operating user travelling to an endpoint by one of two travel routes, according to an embodiment. Environment 200a of FIG. 2A includes a user 202a corresponding generally to user 102 of FIG. 1, such as an operator of a vehicle 204a, which includes or has an associated vehicle device corresponding generally to vehicle device 110 of FIG. 1.

In environment 200a, user 202a wishes to travel to an endpoint 262a in vehicle 204a. When first attempting to use vehicle 204a, user 202a may be detected in vehicle 204a, such as through a sensor in a door, seat, steering wheel, or other location in the car. User 202a may also be detected when logging in to an onboard computing device (e.g., vehicle device 110 of FIG. 1) of vehicle 204a, or may be detected when a device for user 202a is detected by the onboard computing device (e.g., through a device connection). Once user 202a is detected, the onboard computing device may determine an identity of user 202a so that the onboard computing device may determine restrictions placed on user 202a's use of vehicle 204a and associated devices/services. For example, user 202a's identity may be determined through an identifier sent by user 202a's device to the onboard computing device, through a log in process by user 202a with the onboard computing device, and/or through a biometric reading/detection taken of user 202a. Once identification information for user 202a is confirmed, the onboard computing device may access restrictions on user 202a's use of vehicle 204a from a local database or an online database/service associated with vehicle 204a. Restrictions may also be determined from the aforementioned sources by the onboard computing device based on parameters for user 202a in the identification information. For example, if the identification information includes an age, height, health concern/issue, weight, preference (e.g., preference for use of vehicle 204a), or other user parameter, the onboard computing device may use such user parameter (s) in order to determine restrictions associated with the user parameter(s).

As previously discussed, restrictions placed on user 202a's use of vehicle 204a may correspond to restrictions on the use and/or performance of vehicle 204a, vehicle 204a's onboard computing device, user 202a's personal device while operating vehicle 204a, and/or services associated with vehicle 204a. For example, one such restriction would be to bar user 202a from utilizing the onboard computing device's messaging and/or media exchange application, or such applications on user 202a's personal device. Thus, while travelling to endpoint 262a, user 202a may be barred from such services. Another restriction may be placed on passengers allowed to be present in vehicle 204a when user 202a is operating vehicle 204a. For example, a state's driving regulatory laws may prevent new drivers or drivers under a certain age from travelling with passengers or passengers whom do not meet certain criteria. Thus, a restriction may prevent user 202a from travelling with such passengers. Restrictions may also be placed on usage of the onboard computing system's and/or vehicle 204a's associated services. For example, vehicle 204a may utilize a payment provider to complete payment for items, such as food while travelling, gas, vehicle maintenance, tolls, etc. A restriction may be placed on usage of such a payment service by user 202a where the person/entity exerting control over vehicle 204a does not wish to complete payments for user 202a's use of vehicle 204a. Thus, where a location 260a or a location 260b include purchasable items/services for vehicle 204a, user 202a may be prevented from utilizing a payment service associated with vehicle 204a from purchasing items at location 260a or location 260b.

In further embodiments, restrictions may be placed on a travel route, speed, and/or time of travel by user 202a using vehicle 204a. For example, user 202a may travel to endpoint 262a through location 260a or location 260b. A restriction may be placed on user 202a to utilize the travel route through location 260a over location 260b since the route is more direct to endpoint 262a. The restriction may also be placed on the time of day, such that user 202a is required to use the travel route through location 262b during late night or early morning hours even if the travel route is longer as it may be more safe. Moreover, if the person/entity exerting control over vehicle 204a wishes to have user 202a complete a purchase at location 260a or location 260b, the restriction may choose one of the travel routes through location 260a or location 260b.

Figure 2B:
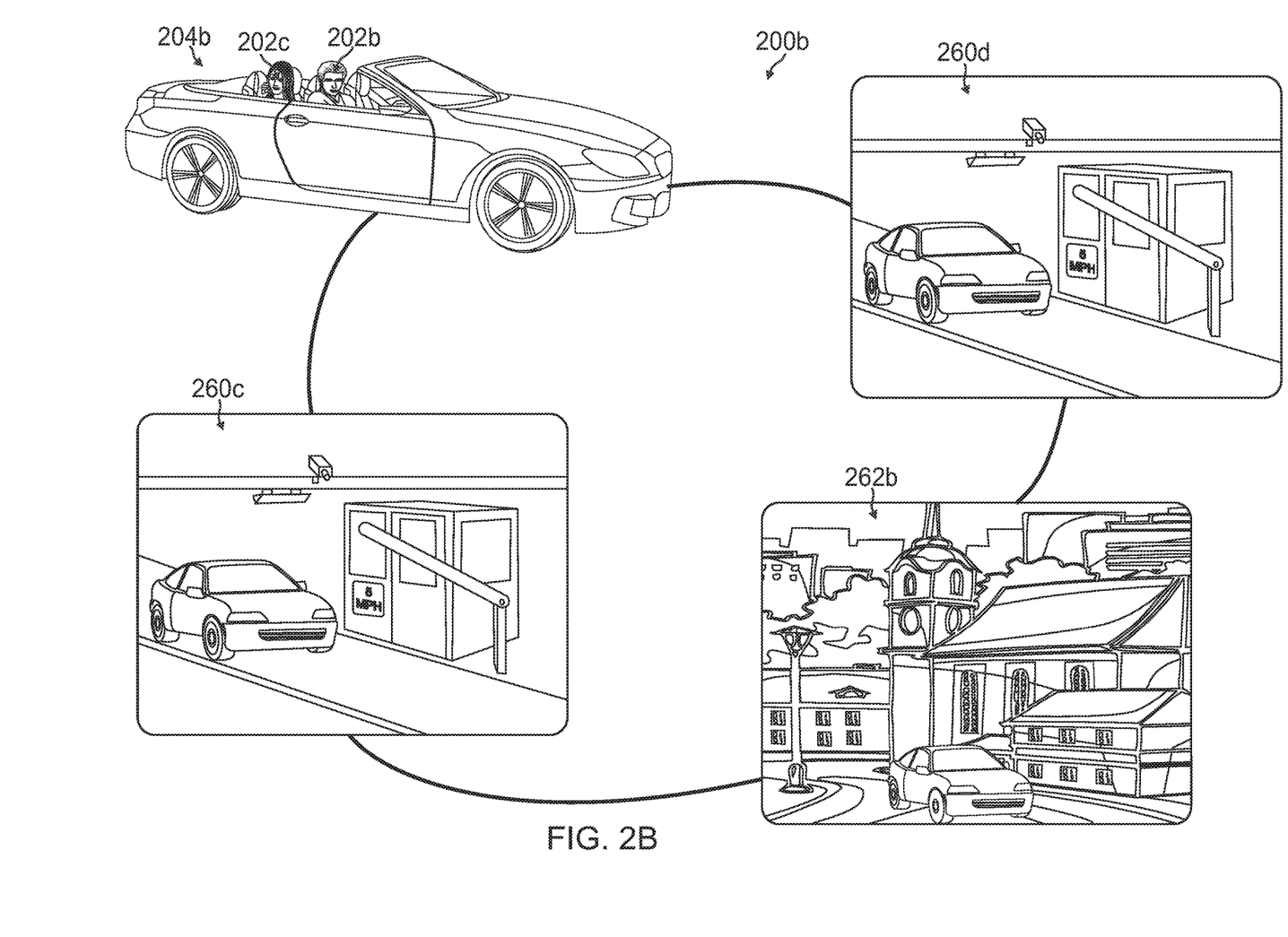
FIG. 2B is an exemplary environment having a vehicle with an operating user and a passenger user travelling to an endpoint by one of two travel routes, according to an embodiment.

FIG. 2B is an exemplary environment having a vehicle with an operating user and a passenger user travelling to an endpoint by one of two travel routes, according to an embodiment. Environment 200a of FIG. 2B includes a user 202b corresponding generally to user 102 of FIG. 1. User 202b may correspond to an operator of a vehicle 204b, which includes or has an associated vehicle device corresponding generally to vehicle device 110 of FIG. 1. Additionally, user 202b may travel with a passenger 202c in vehicle 202b.

In environment 200b, user 202b is travelling in vehicle 204b with passenger 202c. Passenger 202c may be associated with one or more restrictions placed on user 202b's usage of vehicle 204b. For example, where user 202b is prevented from utilizing vehicle 204b without passenger 202c's presence, passenger 202c may be required to be detected and identified in vehicle 204b prior to user 202b's usage of vehicle 204b. Conversely, user 202b may be prevented from utilizing vehicle 204b while passenger 202c is present. Thus, if passenger 202c is detected and/or identified in vehicle 204b, user 202b may be prevented from utilizing vehicle 204b (e.g., vehicle 204b may not start or the person/entity exerting control over vehicle 204b may be alerted).

Passenger 202c may also remove certain restrictions from user 202b's usage of vehicle 204b. For example, user 202b may be prevented from using a payment service associated with vehicle 204b at a location 260c or location 260d. However, if passenger 202c is present in vehicle 204b, the restriction may be removed (e.g., passenger 202c may provide authorization and/or authentication of charges at a merchant, gas station, car maintenance location, toll, etc.). In other embodiments, user 202b may be allowed to travel a route only if passenger 202c if present. In such embodiments, user 202b may be prevented from taking a travel route through location 260d where passenger 202c is not present, thereby being forced to drive through location 260c. However, once passenger 202c is detected and/or identified in vehicle 204b, user 202b may travel through location 260d using vehicle 204b.

Figure 3:
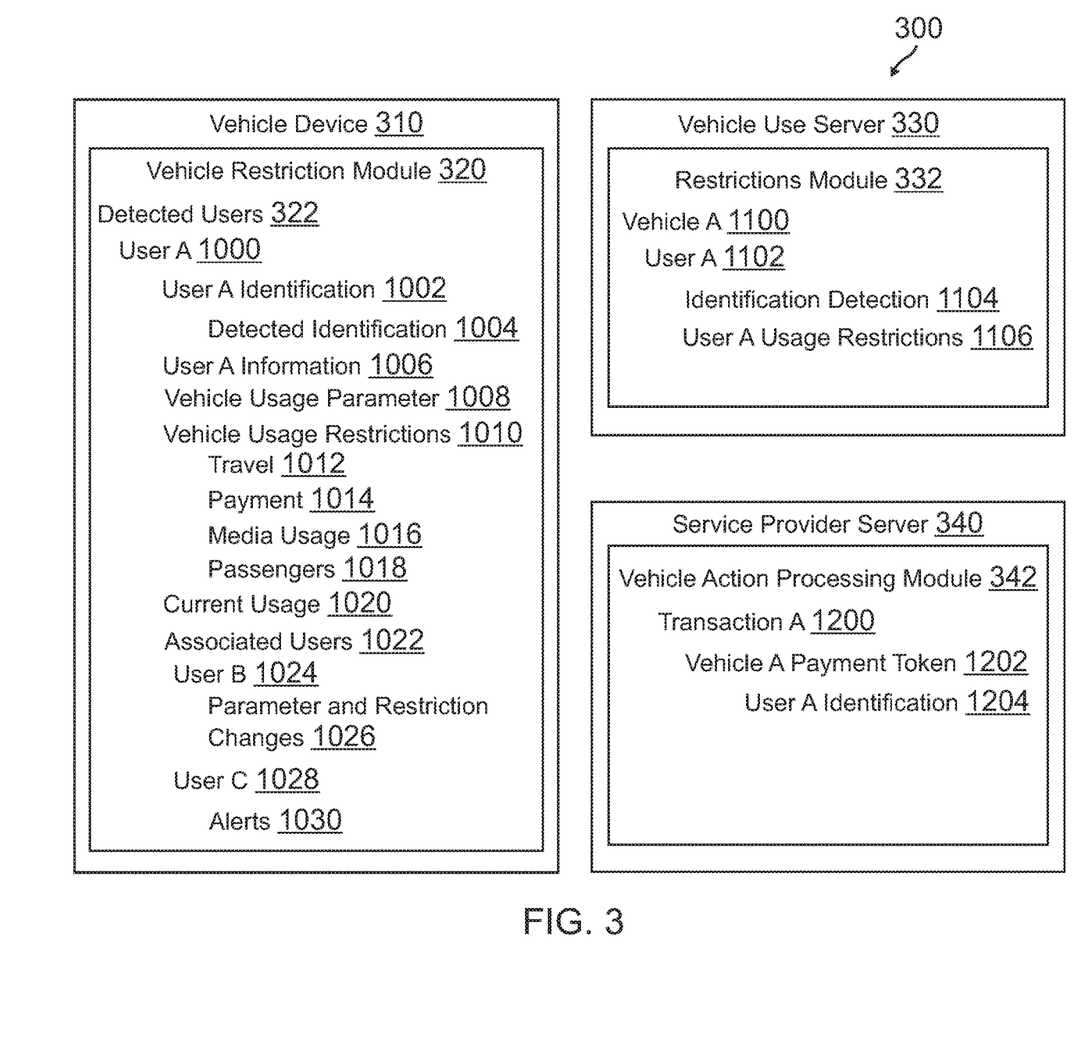
FIG. 3 is an exemplary system environment having restrictions on use of a vehicle by a detected user in the vehicle, according to an embodiment.

FIG. 3 is an exemplary system environment having restrictions on use of a vehicle by a detected user in the vehicle, according to an embodiment. Environment 300 of FIG. 3 includes a vehicle device 310, a vehicle use server 330, and a service provider server 340 corresponding generally to vehicle device 110, vehicle user server 130, and service provider server 140, respectively, of FIG. 1.

Vehicle device 310 executes a vehicle restriction module 320 corresponding generally to the specialized hardware and/or software modules and processes described in reference to vehicle restriction module 120 of FIG. 1. In this regard, vehicle restriction module 320 may be utilized to access and/or determine restrictions for a user (not shown) of a vehicle (not shown) associated with vehicle device 310. The restrictions for the user may be accessed and/or determined after the user is detected in or nearby the vehicle and attempting to operate the vehicle, as previously discussed. Once the user is detected, identification information for the user may be determined and the restrictions may be accessed and/or determined.

Vehicle restriction module 320 includes detected users 322 having a user A 1000. User A 1000 includes information for a user A identification 1002, user A information 1006, a vehicle usage parameter 1008, vehicle usage restrictions 1010, current usage 1020, and associated users 1022. User A identification 1002 includes identification information for user A used to identify user A, which may include detected identification 1004, such as a log in, a detected/connected device and received identifier, and/or a biometric reading for user A. Using user A identification 1002, user A information 1006 may be determined, which may include information about parameters for user A, such as a height, weight, age, health condition, etc. Thus, using user A identification 1002 and/or user A information 1006, vehicle usage parameter 1008 and vehicle usage restrictions 1010 may be accessed/determined. Vehicle usage parameter 1008 may correspond to a restriction on use of the vehicle associated with a user parameter in user A information 1006. Similarly, vehicle usage restrictions 1010 may be accessed based on user A identification 1002, and may include the restriction in vehicle usage parameter 1008 determined through user A information 1006.

Vehicle usage restrictions 1010 includes one or more restrictions on use of the vehicle, such as restrictions on travel 1012 (e.g., a travel time, route, speed, etc.), payment 1014 (e.g., use of an associated payment service to complete payments with merchants, toll operators, service providers, gas stations, and/or vehicle repair/maintenance providers), media usage 1016 (e.g., radio, satellite, communication/messaging/phone services, social networking services, mapping services, etc.), and/or passengers 1018 (e.g., allowed passenger identification, number, age, etc. in the vehicle). Vehicle usage restrictions 1010 may further be communicated to user A when utilizing the vehicle and/or may be enforced on usage of the vehicle by user A.

During user A's usage of the vehicle, the usage may be recorded as current usage 1020. Current usage 1020 may be utilized to determine if user A is operating the vehicle in an unauthorized manner. Current usage 1020 may be communicated to user A and/or a person/entity exerting control over the vehicle. Moreover, while utilizing the vehicle, associated users 1022 may be utilized to either change parameters or alert another user of current usage 1020. In this regard, associated users 1022 include user B 1024 that may travel in the vehicle with user A. User B 1024 includes parameter and restriction changes 1026, which may alert user A's parameters and therefore vehicle usage parameter 1008. Parameter and restriction changes 1026 may change vehicle usage restrictions 1010 so that user A may perform certain actions with respect to the vehicle that user A would be prevented from without user B 1024 being detected and/or identified. Associated users 1022 may further include a user C 1028 having alerts 1030 that may include information in current usage 1020 that vehicle restriction module 320 may communicate to user C 1028 (e.g., unauthorized usage of the vehicle).

Vehicle use server 330 include a restrictions module 322 corresponding generally to the specialized hardware and/or software modules and processes described in reference to restrictions module 132 of FIG. 1. In this regard, restrictions module 332 includes a vehicle A 1100 setting for restrictions of a vehicle A. Restrictions for vehicle A 1100 may be general, or also may have particular settings under a user A 1102. Thus, user A 1102 includes information for identification detection 1104 of user A and user A usage restrictions 1106. Thus, user A 1102 includes information allowing vehicle device 110 to identify user A and determine restrictions in user A usage restrictions 1106. Restrictions for vehicle A 1100 may be communicated to vehicle device 310 for storage, or may be accessed be vehicle restriction module 320 on detection/identification of user A.

Service provider server 340 include a vehicle action processing module 342 corresponding generally to the specialized hardware and/or software modules and processes described in reference to vehicle action processing module 142 of FIG. 1. In this regard, service provider server 340 may be utilized to process one or more actions of user A while operating the vehicle corresponding to vehicle device 310 based on restrictions set on user A's usage of the vehicle. Thus, vehicle action processing module 342 includes a transaction A 1200, such as a payment transaction for purchase of some item and/or service. Transaction A 1200 includes a vehicle A payment token 1202 having identification of the payment account/instrument corresponding to vehicle A and utilized to complete transaction a 1200. Transaction A 1200 may further include user A identification 1204 as additional identification of the person requesting transaction A 1200.

Figure 4:
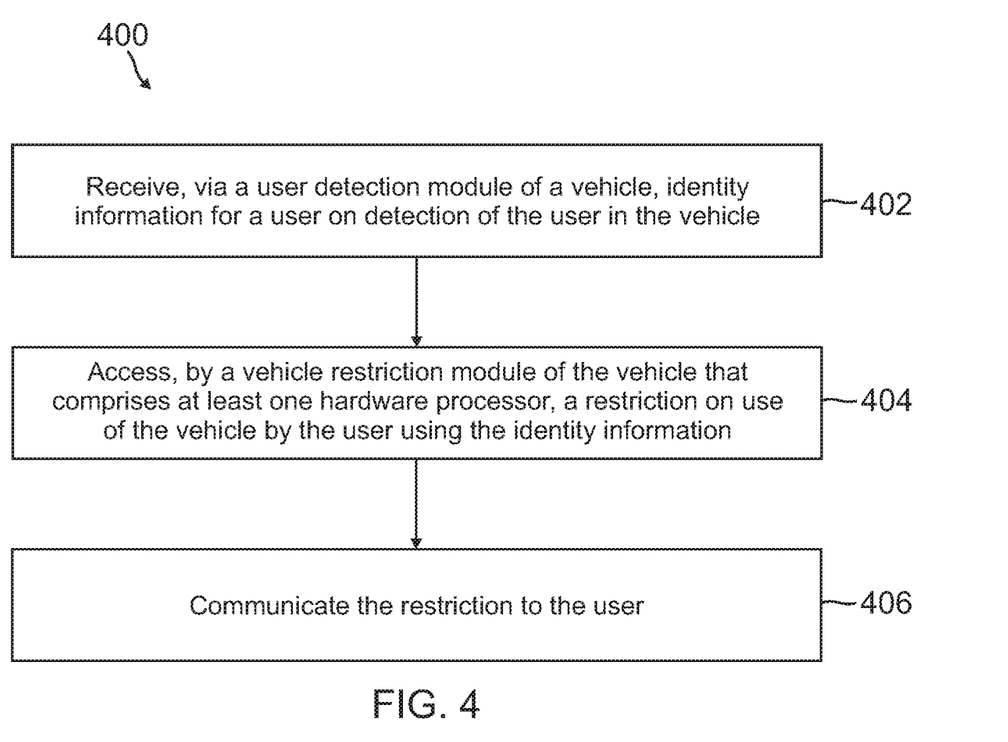
FIG. 4 is a flowchart of an exemplary process for vehicle use and performance restrictions based on detected users, according to an embodiment.

FIG. 4 is a flowchart of an exemplary process for vehicle use and performance restrictions based on detected users, according to an embodiment. Note that one or more steps, processes, and methods described herein may be omitted, performed in a different sequence, or combined as desired or appropriate.

At step 402, identity information for a user is received on detection of the user in the vehicle via a user detection module of the vehicle. The user detection module may comprise a wireless beacon utilizing a short range communication protocol to connect with a device associated with the user when the device is in proximity to at least one of the vehicle and the user detection module. The short range communication protocol may comprise one of near field communication, radio communication, infrared communication, Bluetooth communication, Bluetooth Low Energy (BLE) communication, LTE Direct communication, and WiFi communication. The user detection module may detect the user using one of a weight sensor, door sensor, a login on an onboard computing system, a fingerprint scanner, a retinal scanner, a movement sensor, and a microphone. The user detection module may determine the identity information using at least one of a weight of the first user, a login of the first user on an onboard computing system, an RFID tag, a radio or infrared communication from a key unit, and a biometric of the first user.

A restriction on use of the vehicle by the user is accessed using the identity information by a vehicle restriction module of the vehicle that comprises at least one hardware processor, at step 404. At step 406, the restriction is communicated to the user. The restriction may be communicated to the user by at least one of an alert on a display interface of a display module in the vehicle and a message to a communication device of the user, for example, from a communication module of the vehicle. The vehicle restriction module may monitor the use of the vehicle by the user to determine if the use of the vehicle by the user complies with the restriction. The vehicle restriction module may enforce the restriction on the use of the vehicle by the user if the use of the vehicle by the user does not comply with the restriction. The vehicle restriction module may alert at least one of the user and a second user associated with at least one of the user and the vehicle if the use of the vehicle by the user does not comply with the restriction.

The vehicle restriction module may further process the restriction to determine a usage of the vehicle, for example, by enforcing the restriction on use or performance of the vehicle by the user. The use or performance of the vehicle may comprise at least one of a travel route taken by the vehicle, a speed limit of the vehicle, an onboard computing feature of the vehicle, and an onboard service of the vehicle. Thus, the restriction may comprise a restriction on at least one of travel distance using the vehicle, travel route using the vehicle, travel speed using the vehicle, an item payment made using an onboard computing device of the vehicle, a toll payment made using the onboard computing device of the vehicle, media playback using the onboard computing device of the vehicle, radio or media stations available using the onboard computing device of the vehicle, use of a communication application of the onboard computing device of the vehicle, a number of other passengers in the vehicle, an age of the other passengers in the vehicle, an identity of the other passengers in the vehicle, and an insurance policy associated with the vehicle. For example, the restriction may be at least one of health based, age based, spending based, and insurance based.

A second user may set the restriction using the vehicle restriction module. In other embodiments, the second user sets the restriction with one of a service provider associated with the vehicle, a cloud storage service associated with the vehicle, and a device associated with the first user, and the vehicle restriction module may determine the restriction by receiving or accessing the restriction from the one of the service provider, the cloud storage, and the device. The vehicle restriction module may receive at least one second use restriction comprising an update to the restriction and process the at least one second use restriction to determine another usage of the vehicle by the user. The user detection module may also detect a second user in the vehicle when the user utilizes the vehicle and determine a second identification for the second user. In such embodiments, the vehicle restriction module may process the second identification to determine any changes to the restriction caused by detecting the second user in the vehicle with the user. For example, the second user may comprise at least one of a guardian of the user, an owner of the vehicle, and a manager of an insurance policy associated with the vehicle.

Figure 5:
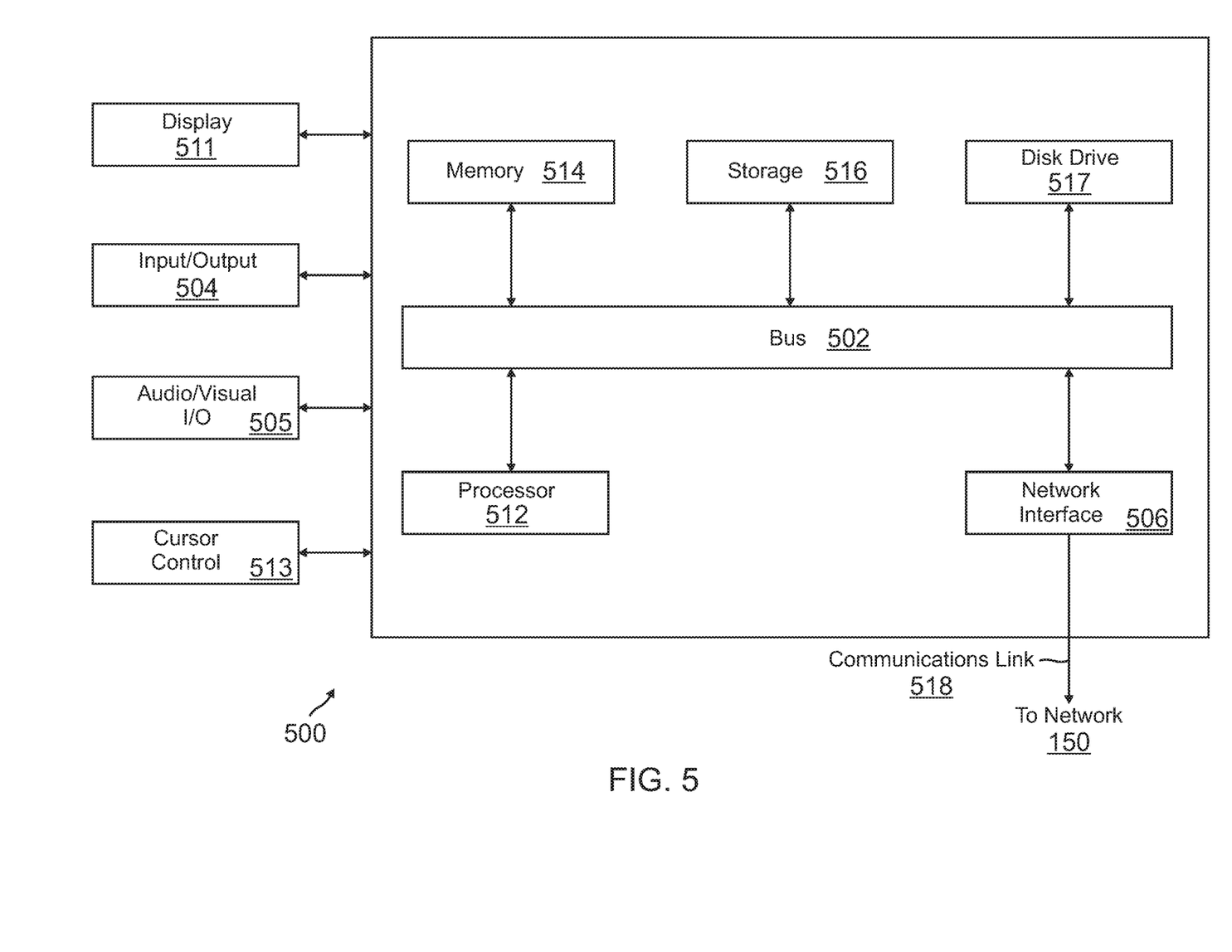
FIG. 5 is a block diagram of a computer system suitable for implementing one or more components in FIG. 1, according to an embodiment.

FIG. 5 is a block diagram of a computer system suitable for implementing one or more components in FIG. 1, according to an embodiment. In various embodiments, the user device may comprise a personal computing device (e.g., smart phone, a computing tablet, a personal computer, laptop, a wearable computing device such as glasses or a watch, Bluetooth device, key FOB, badge, etc.) capable of communicating with the network. The service provider may utilize a network computing device (e.g., a network server) capable of communicating with the network. It should be appreciated that each of the devices utilized by users and service providers may be implemented as computer system 500 in a manner as follows.

Computer system 500 includes a bus 502 or other communication mechanism for communicating information data, signals, and information between various components of computer system 500. Components include an input/output (I/O) component 504 that processes a user action, such as selecting keys from a keypad/keyboard, selecting one or more buttons, image, or links, and/or moving one or more images, etc., and sends a corresponding signal to bus 502. I/O component 504 may also include an output component, such as a display 511 and a cursor control 513 (such as a keyboard, keypad, mouse, etc.). An optional audio input/output component 505 may also be included to allow a user to use voice for inputting information by converting audio signals. Audio I/O component 505 may allow the user to hear audio. A transceiver or network interface 506 transmits and receives signals between computer system 500 and other devices, such as another user device, service device, or a service provider server via network 150. In one embodiment, the transmission is wireless, although other transmission mediums and methods may also be suitable. One or more processors 512, which can be a micro-controller, digital signal processor (DSP), or other processing component, processes these various signals, such as for display on computer system 500 or transmission to other devices via a communication link 518. Processor(s) 512 may also control transmission of information, such as cookies or IP addresses, to other devices.

Components of computer system 500 also include a system memory component 514 (e.g., RAM), a static storage component 516 (e.g., ROM), and/or a disk drive 517. Computer system 500 performs specific operations by processor(s) 512 and other components by executing one or more sequences of instructions contained in system memory component 514. Logic may be encoded in a computer readable medium, which may refer to any medium that participates in providing instructions to processor(s) 512 for execution. Such a medium may take many forms, including but not limited to, non-volatile media, volatile media, and transmission media. In various embodiments, non-volatile media includes optical or magnetic disks, volatile media includes dynamic memory, such as system memory component 514, and transmission media includes coaxial cables, copper wire, and fiber optics, including wires that comprise bus 502. In one embodiment, the logic is encoded in non-transitory computer readable medium. In one example, transmission media may take the form of acoustic or light waves, such as those generated during radio wave, optical, and infrared data communications.

Some common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EEPROM, FLASH-EEPROM, any other memory chip or cartridge, or any other medium from which a computer is adapted to read.

In various embodiments of the present disclosure, execution of instruction sequences to practice the present disclosure may be performed by computer system 500. In various other embodiments of the present disclosure, a plurality of computer systems 500 coupled by communication link 518 to the network (e.g., such as a LAN, WLAN, PTSN, and/or various other wired or wireless networks, including telecommunications, mobile, and cellular phone networks) may perform instruction sequences to practice the present disclosure in coordination with one another.

Where applicable, various embodiments provided by the present disclosure may be implemented using hardware, software, or combinations of hardware and software. Also, where applicable, the various hardware components and/or software components set forth herein may be combined into composite components comprising software, hardware, and/ or both without departing from the spirit of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

The foregoing disclosure is not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, persons of ordinary skill in the art will recognize that changes may be made in form and detail without departing from the scope of the present disclosure. Thus, the present disclosure is limited only by the claims.

What is claimed is:

1. A vehicle device system comprising:
 a non-transitory memory; and
 one or more hardware processors coupled to the non-transitory memory and configured to read instructions from the non-transitory memory to cause the vehicle device system to perform operations comprising:
  connecting with a mobile device of a first user through short range wireless communications when the mobile device is within a proximity range of the vehicle device system for a vehicle;
  determining an identifier of the first user from the mobile device;
  determining a first restriction on a use of the vehicle by the first user using the identifier;
  implementing the first restriction during the use of the vehicle;
  receiving a modification to the first restriction from a user device of a second user; and
  adjusting the first restriction during the use of the vehicle based on the modification.

2. The vehicle device system of claim 1, wherein the operations further comprise:
 detecting that the user device of the second user is one of within the proximity range of the vehicle device system or has left the proximity range of the vehicle device system,
 wherein the modification is received in response to the detecting.

3. The vehicle device system of claim 2, wherein the modification on the first restriction comprises one of a further limitation on the first restriction or a removal of a limitation of the first restriction, and wherein the modification is based on the second user being within the vehicle or the second user exiting the vehicle.

4. The vehicle device system of claim 2, wherein the operations further comprise:

requesting the modification from the user device of the second user in response to the detecting,
wherein the modification is received in response to the requesting.

5. The vehicle device system of claim 1, wherein the first restriction comprises one of a driving restriction during the use of the vehicle by the first user, a device restriction on one of the mobile device or the vehicle device system during the use of the vehicle, or a payment restriction on a payment made via the vehicle device system during the use of the vehicle.

6. The vehicle device system of claim 1, wherein prior to the connecting, the operations further comprise:
receiving the first restriction from the user device of the second user; and
storing the first restriction with the identifier for the second user.

7. The vehicle device system of claim 1, wherein the operations further comprise:
receiving a second restriction on the vehicle during the use; and
implementing the second restriction during the use of the vehicle.

8. The vehicle device system of claim 7, wherein the operations further comprise:
displaying the first restriction and the second restriction via one of a heads-up display or a console display of the vehicle device system during the use.

9. The vehicle device system of claim 1, wherein the operations further comprise:
monitoring an operation of the vehicle by the second user during the use; and
determining, based on the operation, whether the use complies with at least one of the first restriction or the modification.

10. The vehicle device system of claim 9, wherein the operations further comprise:
notifying the user device associated with the second user based on the monitoring.

11. A method comprising:
receiving restriction data for a vehicle usage restriction from a first device of a first user, wherein the restriction data comprises a process that limits a usage of a vehicle by a second user via a vehicle console computing device of the vehicle;
receiving an identifier associated with the second user, wherein the identifier identifies the second user to the vehicle console computing device;
storing the restriction data and the identifier;
detecting the identifier via the vehicle console computing device; and
setting, using the vehicle console computing device, the vehicle usage restriction during the usage of the vehicle by the second user using the restriction data.

12. The method of claim 11, wherein the vehicle usage restriction comprises one of an audio component restriction on audio provided during the usage of the vehicle, a mobile phone usage restriction during the usage of the vehicle, or a payment limit on a payment provided during the usage of the vehicle.

13. The method of claim 11, further comprising:
outputting the vehicle usage restriction to the second user during the usage of the vehicle.

14. The method of claim 11, wherein the detecting the identifier comprises receiving short range wireless communication information for a short range wireless connection between a second device of the second user and the vehicle console computing device, wherein the short range wireless communication information comprises the identifier.

15. The method of claim 14, further comprising:
detecting a disconnection of the short range wireless connection between the second device and the vehicle console computing device; and
removing the vehicle usage restriction on the vehicle based on the disconnection.

16. The method of claim 14, further comprising:
monitoring the usage of the vehicle by the second user during the short range wireless connection.

17. The method of claim 16, further comprising:
notifying the first device if the monitoring the usage indicates that the usage of the vehicle by the second user does not meet the vehicle usage restriction or the usage of the vehicle by the second user indicates an attempted usage of the vehicle that violates the vehicle usage restriction.

18. The method of claim 16, wherein the monitoring comprises receiving data via a sensor of the vehicle, and wherein the sensor comprises one of a door sensor, a weight sensor, a pressure sensor, a key detection sensor, a biometric scanner, a camera, a microphone, or a proximity sensor.

19. A non-transitory machine-readable medium having stored thereon machine-readable instructions executable to cause a machine to perform operations comprising:
receiving, by a communication device of a first user from a vehicle device, vehicle usage information during an operation of a vehicle by a second user based on an identifier for the second user received from the vehicle device, wherein the operation of the vehicle is limited by a restriction on the operation set by the first user with the vehicle device;
receiving, by the communication device, a modification to the restriction on the operation from the first user, wherein the modification changes the restriction during the operation by the second user; and
modifying the restriction with the vehicle device based on the modification and the identifier for the second user.

20. The non-transitory machine-readable medium of claim 19, wherein the operations further comprise:
notifying the second user of the modification via the vehicle device.

* * * * *